(12) United States Patent
Yamaguchi et al.

(10) Patent No.: US 9,132,036 B2
(45) Date of Patent: Sep. 15, 2015

(54) STRIPPING KNIFE

(75) Inventors: Akio Yamaguchi, Utsunomiya (JP);
Masatoshi Fukuda, Utsunomiya (JP);
Masahiko Saito, Utsunomiya (JP)

(73) Assignee: MANI, INC., Utsunomiya-shi, Tochigi (JP)

( * ) Notice: Subject to any disclaimer, the term of this patent is extended or adjusted under 35 U.S.C. 154(b) by 0 days.

(21) Appl. No.: 12/597,384

(22) PCT Filed: Apr. 25, 2008

(86) PCT No.: PCT/JP2008/058073
§ 371 (c)(1),
(2), (4) Date: Jun. 17, 2010

(87) PCT Pub. No.: WO2008/136410
PCT Pub. Date: Nov. 13, 2008

(65) Prior Publication Data
US 2010/0280535 A1 Nov. 4, 2010

(30) Foreign Application Priority Data
Apr. 27, 2007 (JP) .................................. 2007-119126

(51) Int. Cl.
*A61F 9/007* (2006.01)
*A61B 17/3211* (2006.01)
*A61F 9/013* (2006.01)

(52) U.S. Cl.
CPC ........... *A61F 9/0133* (2013.01); *A61B 17/3211* (2013.01)

(58) Field of Classification Search
CPC .............. A61F 9/0133; A61F 9/00754; A61B 17/3211; B26B 3/00; B26B 3/02; B26B 9/02

USPC .......................................... 606/166, 167, 107
See application file for complete search history.

(56) References Cited

U.S. PATENT DOCUMENTS

| | | | | |
|---|---|---|---|---|
| 5,224,950 A | * | 7/1993 | Prywes | 606/166 |
| 5,601,584 A | * | 2/1997 | Obagi et al. | 606/172 |
| 5,713,915 A | * | 2/1998 | Van Heugten et al. | 606/166 |
| 6,837,896 B2 | * | 1/2005 | Matsutani et al. | 606/167 |
| 7,648,516 B2 | * | 1/2010 | Matsutani et al. | 606/166 |
| 2003/0088258 A1 | | 5/2003 | Feaster | |
| 2004/0073303 A1 | * | 4/2004 | Schanzlin et al. | 606/166 |
| 2004/0089159 A1 | * | 5/2004 | Matsutani et al. | 99/339 |

(Continued)

FOREIGN PATENT DOCUMENTS

JP 9-276284 A 10/1997
JP 2005-021321 A 1/2005

(Continued)

*Primary Examiner* — Sarah W Aleman
(74) *Attorney, Agent, or Firm* — Shlesinger, Arkwright & Garvey LLP

(57) ABSTRACT

[Problems] To ensure the sharpness of a stripping knife whereby a part of a living tissue is incised and stripped while preventing a cut along the thickness direction.
[Means for Solving Problems] A stripping knife (A) having a plate-shaped blade (3) having an edge (1) around the periphery, a shank (5) connected to the blade (3), and a handle (7) holding the shank (5) in the integrated state, wherein the blade (3) is composed of the edge (1) formed at the front end and a guide face (2) which is formed between the edge (1) and the front face (3b) of the connected plate constituting the blade (3) and brought into contact with the surface (13) of the remaining tissue.

2 Claims, 4 Drawing Sheets

(56) References Cited

U.S. PATENT DOCUMENTS

2004/0230210 A1* 11/2004 Carriazo ................. 606/166
2004/0260320 A1* 12/2004 Lisk et al. ............... 606/166
2005/0004588 A1* 1/2005 Saito et al. .............. 606/167
2006/0206126 A1 9/2006 Sugimura et al.

FOREIGN PATENT DOCUMENTS

| | | |
|---|---|---|
| JP | 2005-334054 A | 12/2005 |
| JP | 2006-239409 A | 11/2006 |

* cited by examiner (a)

(b)

STRIPPING KNIFE

TECHNICAL FIELD

The present invention relates to a stripping knife used for stripping a part of tissue from a living body.

BACKGROUND ART

There is a surgery that involves thinly stripping a part of a living tissue. Such surgery includes a case where tissue is required to be removed from a living body or where partially stripped tissue is not removed and allowed to remain clinging to the living body after surgery. In both the cases, it is preferable that the stripped surface of tissue is as smooth as possible. In particular, it is preferable that a stripped piece is uniform in thickness.

When a tissue part to be stripped is muscle or skin, a surgical knife or similar, which is comparatively easy to manipulate can be used. However, in the case of sites such as a blood vessel or eyeball sclera, the area of tissue to be stripped is small and, therefore, a knife with a very small blade is used.

It is preferable that a knife for stripping a part of tissue cut sharply. However, in view of the specialty of stripping tissue so thinly, a problem is raised; that is, a too sharp knife may cut tissue in the depth direction, so it may be required to correct manipulation at each time, which may result in a roughness of the stripped surface, thereby making it difficult to obtain a smooth surface.

For example, in surgery for glaucoma, Schlemm's canal is incised and aqueous humor is discharged, thereby reducing ocular tension. Schlemm's canal is located near and under the scleral spur. Accordingly, the surgery is performed as follows: the sclera is incised into a substantially rectangular shape except for the side located next to the cornea. Then the sclera is stripped from the incised portion toward the remaining side, thereby forming a valve or flap from the stripped sclera, thus leaving the sclera in the living body.

When stripping sclera as described above, a knife generally called "a golf knife" is used. A golf knife includes: a substantially linear shank attached to a handle; and a plate-shaped blade disposed at the leading end of the shank and has an axis that inclines with respect to the axis of the flat surface of the shank. This knife therefore has a shape similar to a golf club, in a plan view.

The cutting edge of the golf knife is formed at a periphery of the plate-shaped blade. Using this cutting edge, the sclera is incised and the incised site is stripped. This cutting edge has a sharp leading end formed by grinding the periphery of the blade in the direction of the thickness of the blade. Therefore, the cutting edge has a cross-section of triangular in which a sharp leading end is located substantially in the middle in the direction of the thickness from the surfaces of a plate forming the blade.

Sclera has a relatively high strength. Sclera may be stripped by moving the knife sideways in alternate directions. This may result in roughening of the surface of the sclera stripped by the golf knife. Therefore, the golf knife used for stripping sclera is generally buffed or suchlike in order to blunt its edge forcibly.

In cataract surgery, the cornea is incised and a lens is inserted. Generally, the knife used to incise the cornea requires great sharpness (see Patent Document 1, for example).

Heart surgery for removing fat from around a blood vessel also uses a golf knife as described above (in heart surgery, it is generally called a "hockey knife"). In this type of surgery, using the cutting edge of the golf knife, fat adhering to a blood vessel is stripped and collected toward one side.

Patent Document 1: Japanese Patent Application Laid-Open (JP-A) No. 2005-334054

DISCLOSURE OF THE INVENTION

Problems to be Solved by the Invention

Surgery in which sclera is incised or stripped using a golf knife the edge of which has been forcibly blunted has a problem that extra force may be applied to cut the sclera and it is required to manipulate the golf knife finely. This problem is common to the knife when used for stripping tissue in other sites, for example, blood vessel walls.

An object of the present invention is to provide a stripping knife that is sharp and capable of preventing over-cutting in the thickness direction of the tissue.

Means for Solving the Problem

A stripping knife according to the present invention which is directed to solve the foregoing problems is a stripping knife used for stripping tissue, including: a plate-shaped blade having a cutting edge formed at a periphery of the blade; a shank continuously formed from the blade; and a handle holding the shank in an integral state. In this stripping knife, the blade includes the cutting edge formed at the leading end of the blade and a guide face which is formed between the cutting edge and a surface of the plate formed continuously from the cutting edge to form the blade contacts with a surface of the remaining tissue. In addition, the blade may have an axis inclining to the axis of the shank. A guide face may be formed on each side of the blade.

Effect of the Invention

In the stripping knife according to the present invention, when a surgeon incises tissue while gripping and manipulating the handle and stripping an incised site from a living body, one of the guide faces of the blade comes into contact with the surface of the remaining tissue, thereby determining the direction in which the stripping knife is manipulated. When one of the guide faces is brought into contact with the surface of the remaining tissue, the stripping knife enables the edge of the leading end of the cutting edge to be positioned higher than a line extending from this guide face. This prevents the blade from cutting into the living tissue in the depth direction despite the sharpness of the blade. This prevents the blade from roughening the surface of stripped tissue, thus ensuring that the stripped surface of the tissue is smooth. Even in heart surgery, the stripping knife is prevented from cutting into a living body in the depth direction and penetrating a blood vessel.

In addition, the axis of the blade inclines with respect to the axis of the shank. This makes it possible to orient the axis of the blade in a direction opposite to the direction in which a surgeon naturally grips the knife (when the surgeon is located upstream of the direction in which sclera is incised, especially in the case of sclera); in other words, the axis of the blade inclines in a direction canceling the inclination of the handle and shank with respect to the surgery site. Accordingly, unlike a case when the axis of the blade coincides with that of the shank, a surgeon does not have to be in an uncomfortable position in order to orient the handle and shank in the direction in which tissue is to be incised. Thus, the direction of forward movement of the blade and the direction in which tissue is to be incised coincide, so that a surgeon is able to perform surgery easily in a position natural to him or her.

Additionally, guide faces are formed on both sides of the blade. Accordingly, both sides of the blade can be used, and thus even though the axis of the blade incline, smooth surgery is enabled without the need for specifically orienting the direction of forward movement of the blade.

In particular, this makes it possible to improve the sharpness of the cutting edge, thus eliminating an extra force when the stripping knife is manipulated, and thereby enhancing responsiveness. This ensures smooth surgery for stripping a part of tissue from a living body.

EXPLANATIONS OF REFERENCE NUMERALS

Figure 1:
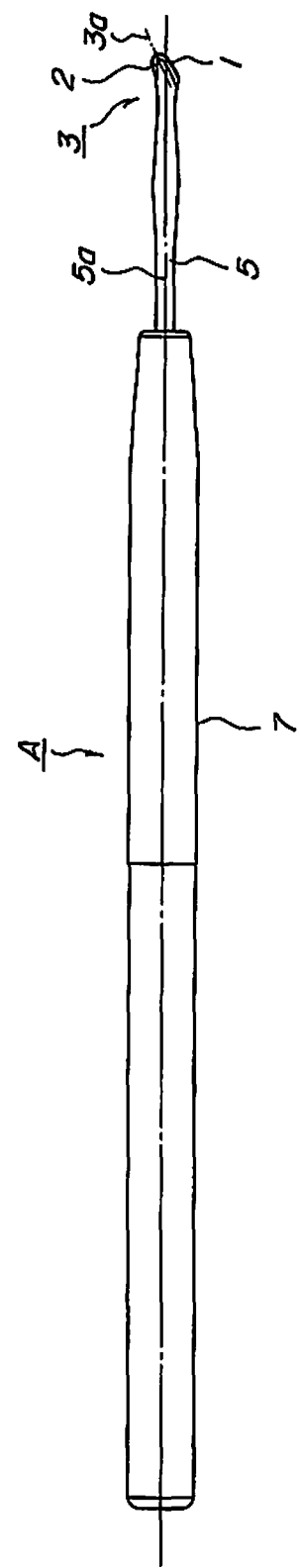
FIG. 1 is a front view of a stripping knife according to a first embodiment.

A Stripping knife
1 Cutting edge
2 Guide face
3 Blade
$3a$ Axis
$3b$ Surface
5 Shank
$5a$ Axis
7 Handle
10 Tissue
11 Stripped tissue
12 Strip point
13 Stripped tissue surface

BEST MODE FOR CARRYING OUT THE INVENTION

Hereinafter will be described the preferred embodiment of a stripping knife according to the present invention. The stripping knife according to the present invention is used for incising a part of tissue on a living body and stripping the incised tissue from the living body. This knife is designed to ensure a smooth stripped surface without degrading sharpness.

The stripping knife according to an embodiment the present invention includes: a plate-shaped blade having a cutting edge formed around its periphery; a shank; and a handle holding the shank in the integrated state. In the present invention, the blade and shank are not limited to a flat shape. In particular, it is preferable that the blade has the optimum shape for the type of tissue to be stripped.

First Embodiment

Figure 2:
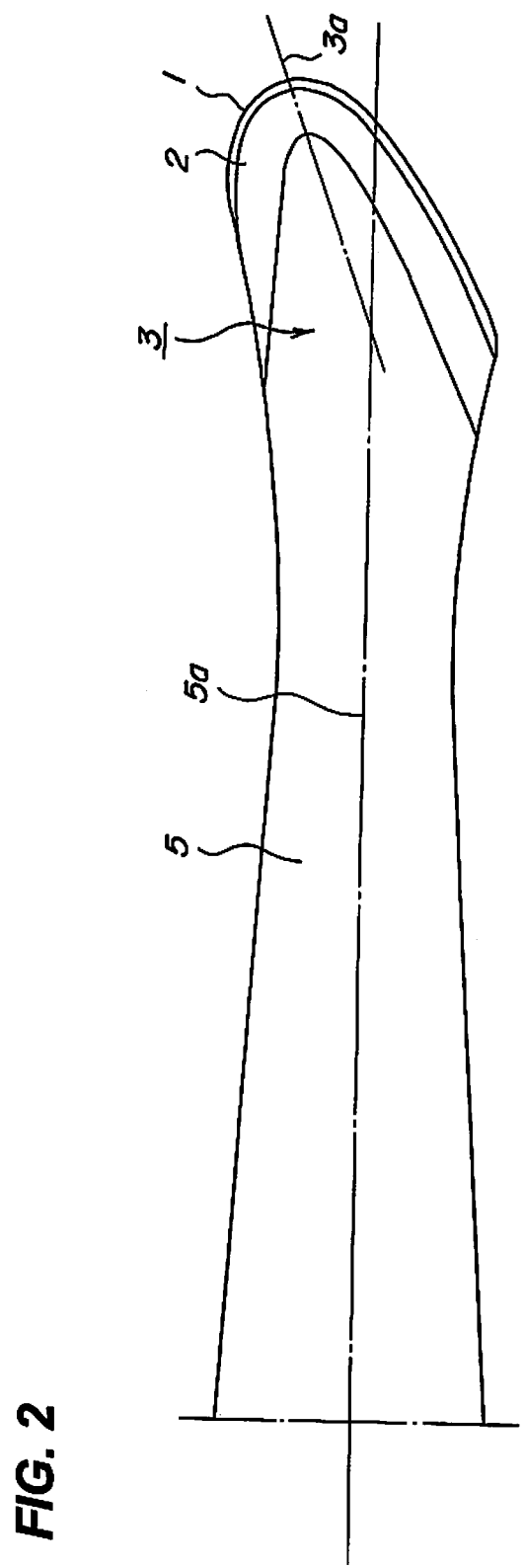
FIG. 2 is an enlarged view of a blade.
Figure 3:
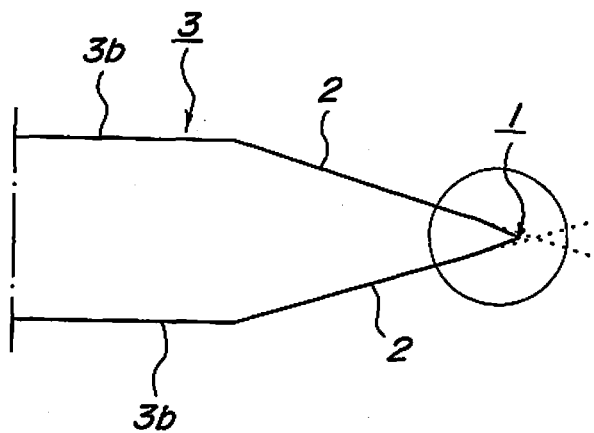
FIG. 3 is an enlarged view of a cross-section along axis $3a$ shown in FIG. 2.
Figure 3:
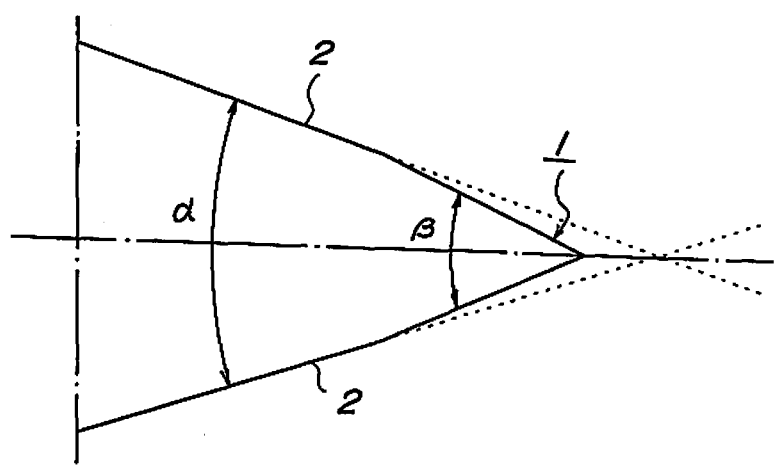
Figure 4:
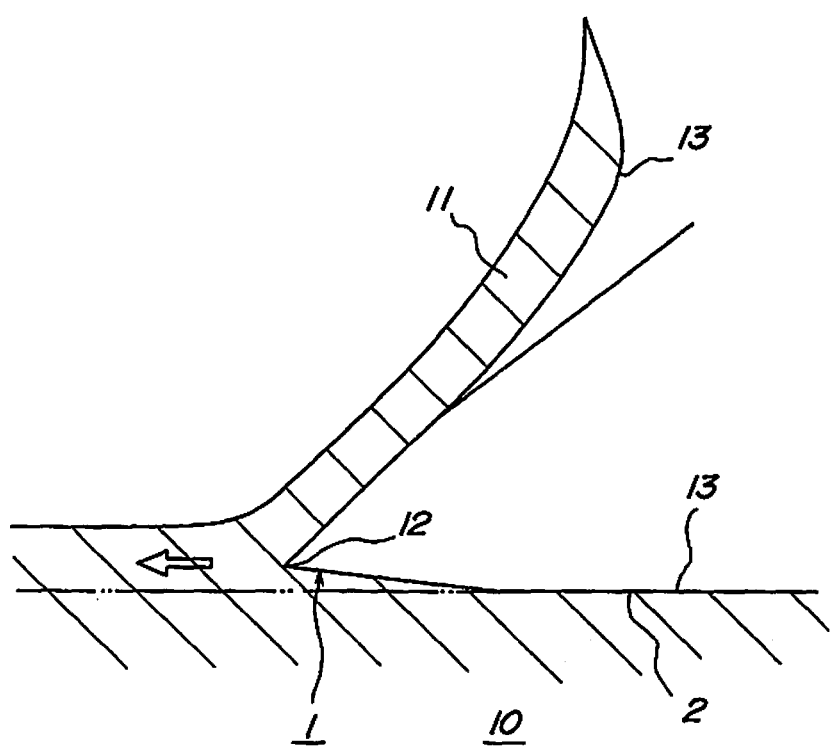
FIG. 4 is an explanatory view of stripping tissue.

The configuration of a stripping knife according to a first embodiment will be described with reference to the drawings. FIG. 1 is a front view of a stripping knife according to the present embodiment. FIG. 2 is an enlarged view of a blade. FIG. 3 is an enlarged view of a cross-section along the axis of the blade shown in FIG. 2. FIG. 4 is an explanatory view of stripping tissue.

The stripping knife A has the same flat shape as that of a knife generally called "a golf knife", which is widely used to incise a part of the sclera in glaucoma treatment and to strip the incised sclera.

The stripping knife A includes: a blade 3 having a cutting edge 1 formed at a periphery thereof and having an edge at the leading end and guide faces 2 formed continuously from the cutting edge 1 on both sides of the blade 3; a shank 5 formed continuously from the blade 3; and a handle 7 holding the shank in an integral state.

Particularly, in the golf knife shown in FIG. 1, the axis $5a$ of the shank 5 coincides with that of the handle 7. However, the blade 3 is located at the leading end of the shank 5 and has an axis $3a$ inclining with respect to the axis $5a$ of the shank 5. The blade 3 has the cutting edge 1 and guide faces 2 around the axis $3a$. Therefore, the blade 3 and the shank 5 together form a shape that looks like a golf club in a plan view. Since the blade 3 has the axis $3a$ inclining with respect to the axis $5a$ of the shank 5, the following positional relation can be established: (especially, when a surgeon is located upstream in the direction in which he or she incises sclera) the axis $3a$ of the blade 3 inclines in the direction opposite to the direction in which the surgeon naturally grips the knife (the axis of the blade 3 inclines in a direction to cancel the inclination of the handle 7 and the axis $5a$ of the shank 5 with respect to the direction in which an surgery site is incised). This prevents such a situation that a surgeon has to be in an uncomfortable position to orient the handle 7 and shank 5 in the direction in which the surgery site is to be incised, as in the case when the blade 3 has the same axis $5a$ of the shank 5. Thus, a surgeon can perform an operation in a natural position since the direction in which the blade 3 moves forward and the direction in which the area to be incised coincide. It is preferable that the axis $3a$ of the blade 3 inclines at an angle of approximately 30° to 40°.

In addition, it is preferable that the curvature radius R of the cutting edge 1 of the periphery of the blade 3 is approximately from 0.45 to 0.7 mm, although it depends on the width of the tissue to be stripped. If R is less than 0.45 mm, the blade 3 may tend to move forward while rotating slightly (to the right or left) around the axis $5a$, or may tend to be stuck into tissue. Accordingly, the guide faces cannot exert there effect even when provided, resulting in a non-uniform stripped surface. If R is greater than 0.7 mm, on the other hand, it is difficult to cope with a small stripping area and degrades the knife's operability.

The blade 3 and the shank 5 are integrally formed of metal. The thus integrated shank 5 is then held in the integrated state with the handle 7. The structure in which the shank 5 is integrated with the handle 7 is not limited to this. When the handle 7 is made of a synthetic resin, the shank 5 may be integrated with the handle 7 by its being insertion-molded into the handle 7, driven into the handle 7, or by adhesion. When the handle 7 is made of metal, the shank 5 and the handle 7 may be integrated by providing a chuck at the leading end of the handle 7 and holding the shank 5 by means of this chuck. In addition, regardless of whether the handle 7 is made of resin or metal, the shank 5 may be integrated with the handle 7 by being screwed into the handle 7.

The handle 7, which is gripped by a doctor for manipulation of the stripping knife, is made of synthetic resin or metal, has a shape that ensures a secure grip, and also has a structure that securely holds the shank 5 in the integrated state. In other words, as long as the handle 7 holds the shank 5 securely and ensures a secure grip of the handle during manipulation of the knife, the material and shape of the handle 7 are not limited. Further, the shank 5 and handle 7 need not be connected directly. A holder for holding the shank 5 may be provided and connected to the handle 7 that allows connection with the holder.

The blade 3 has a plate-like shape. However, the shank 5 is not limited to a plate- or rod-like shape but may have an optimal cross-sectional shape corresponding to the holding structure of the handle 7. When both the blade 3 and shank 5 have a plate-like shape, blanks formed by cut out by press cutting a metal plate may be used as materials to manufacture the blade and shank. When the shank 5 is a round or square rod, the blade 3 may be manufactured by pressing this round or square rod (which is a component of the shank 5 and yet is also used as material for the blade) into a plate shape.

Materials for the blade 3 and shank 5 are not limited to these, and carbon tool or stainless steel may be used. However, since it is not preferable that the blade 3 or shank 5 rust during distribution, austenite stainless steel free from rust is preferred. It is also preferable that the leading end of the blade 3 have a round shape in a plan view, but it may also be polygonal, such as triangular or square.

Additionally, the cutting edge 1 has to be sufficiently sharp to strip living tissue. Therefore, if a metal material expected to be hardened by heat treatment is used, before or after the formation of the cutting edge 1, the metal needs to be hardened by heat treatment at an optimum temperature for the used material. If austenite stainless steel is used, which is not expected to be hardened by heat treatment, it is required to impart a required hardness to the austenite stainless steel by hardening through cold processing. In particular, a material obtained by stretching an austenite texture into the form of fibers by cold-drawing austenite stainless steel wire is preferred because it exhibits great hardness and bending strength.

Each of the guide faces 2 is defined between the cutting edge 1 and the surfaces 3b of the plate-like portion of the blade 3. The function of the guide faces 2 is to guide the stripping knife A in the direction in which the stripping knife A is manipulated (the direction of movement of the stripping knife A), while keeping contacting with the surface of the tissue left in the living body after partial stripping. In the present embodiment, the guide faces 2 are formed on both sides of the blade 3. Additionally, inclination angles of the respective guide faces 2 on both the sides of the blade 3 with respect to the surface 3b of the plate-like portions of the blade 3 are substantially equal. In such a configuration, even when the axis 3a of the blade 3 inclines, the surgeon can reverse the blade 3 to reverse the inclining direction of the blade 3 and still used. This does not restrict the direction of forward movement of the blade 3 to a fixed range, thus enabling smooth surgery.

Accordingly, each of the guide faces 2 are configured to have an angle and a dimension (the distance from its boundary with the cutting edge 1 to the surface 3b of the blade 3) so as to ensure a stable position when a doctor manipulates the stripping knife A. In particular, the angle α (see FIG. 3(*b*)) of each guide face 2 is twice the angle of a surgeon manipulating the stripping knife A with respect to tissue to be stripped, that is, the angle of the stripping knife A with respect to tissue to be stripped.

In the present embodiment, the angle of the stripping knife with respect to the tissue when sclera is the tissue to be stripped falls within the range from 15° to 20° as a result of, for example, the inventor's experiences of actually stripping a sample (the eye balls of pigs, for example) or investigations through interviews. Taking into account this range of angle and the elasticity of the tissue to be removed, the angle α of between each guide face 2 of the stripping knife A is set within the range from 28° to 40°. It is preferable each guide face 2 be sufficiently wider than the cutting edge 1, although it depending on the thickness of the blade 3. In the present invention, the thickness of the blade 3 is 0.3 mm, and the widths of the cutting edge 1 and each guide face 2 along the axis 3a are 0.08 mm and 0.36 mm respectively. Accordingly, in the present embodiment, the ratio of the cutting edge 1 to each guide face 2 is 1:4.5; however, these values are not limited and may be selected according to the thickness of the blade 3 (approximately 1:3 to 7 times, for example).

The angle β of the cutting edge 1 is greater than the angle α between each guide face 2 and is sufficiently sharp to strip tissue. In the present embodiment, it is assumed that the tissue to be stripped is sclera, and the angle at which the stripping knife is able to strip the sclera smoothly has been tested using samples described above. As a result, the angle β is set within the range from 40° to 50°. In addition, when the thickness of the blade 3 is about 0.3 mm, it is preferable that the thickness of the rear end of the cutting edge 1 (the boundary of the cutting edge 1 with each guide face 2) is from 50 to 90 μm. Here, the lower limit 50 μm is used when the angles α and β are 28° and 40° respectively and the ratio of the cutting edge 1 to the guide face 2 is 1:7. And the upper limit 90 μm is used when the angles α and β are 40° and 50° respectively and the ratio of the cutting edge 1 to the guide face 2 is 1:3.

Since the cutting edge 1 and each guide face 2 that have such angles are continuously formed, the leading end of the cutting edge 1 when a tissue 10 is stripped is located higher than a line extending from the guide face 2, as shown in FIG. 4.

Accordingly, when a tissue 10 is incised vertically with the cutting edge 1 or with another knife, thereby defining a incision portion in the thickness direction of the tissue, and then the stripping knife A is moved forward in the direction of arrow (a) from the incision portion while the stripped tissue 11 is gripped upwardly with tweezers, the strip point 12 at which the tissue 10 is being stripped is always located higher than a line extending from the guide face 2 being used. This prevents the stripping knife from cutting the tissue continuously in the depth direction. Additionally, each guide face is set sufficiently wider than the cutting edge 1, thus stabilizing the forward movement of the edges.

Accordingly, when the cutting edge 1 cuts the tissue 10 in the depth direction in the course of stripping the tissue 10, a surgeon does not have to change the position of the stripping knife A in such a manner that the cutting edge 1 faces upward. This prevents the stripped tissue surface 13 from roughening as a result of changes in the position of the stripping knife A, and makes it possible to obtain a nearly smooth stripped tissue surface 13.

The foregoing description is an example when the stripping knife A is used for stripping sclera in ophthalmic surgery. However, the present invention is not limited to use with sclera, but may also be effectively used for stripping other tissues such as fat adhering to a blood vessel. Additionally, the present invention is not limited in coating the blade surfaces with silicon. However, when, for example, sharpness is required, the sharpness may be improved by coating a part of the blade (the side that is not usually used for stripping in the blade, for example) or by coating the entire blade.

INDUSTRIAL APPLICABILITY

A stripping knife according to an embodiment of the present invention is able to ensure the smoothness of the stripped surface of the tissue a part of which is stripped, and is effective for use in stripping tissue in ophthalmic and other surgery.

The invention claimed is:

1. A stripping knife used for stripping tissue, comprising:
a plate-shaped blade having a first face and a second face in a front-back relationship;
a shank formed contiguously with the blade, said shank having a central axis; and
a handle in communication with an end of the shank, so as to hold the shank in an integrated state,
wherein the plate-shaped blade includes:
a first surface formed in the first face,
a second surface which is formed in the second face and is disposed opposite the first surface,
a first guide face which is formed in the first face, is formed contiguously with the first surface and is inclined to the first surface,
a second guide face which is formed in the second face, disposed opposite the first guide surface, is formed contiguously with the second surface and is inclined to the second surface,
a first end surface which is formed in the first face, is formed contiguously with the first guide face and is inclined to the first guide face,
a second end surface which is formed in the second face, is formed contiguously with the second guide face and is inclined to the second guide face, and
a cutting edge formed at an intersection of the first end surface and second end surface, and wherein
an angle β between the first end surface and the second end surface is greater than an angle α between the first guide face and the second guide face, the angle α between the first guide face and the second guide face is from about 28° to 40°, the angle β between the first end surface and the second end surface is from about 40° to 50°, and a ratio of a width of the first end surface in a lengthwise, axial direction of the blade to a width of the first guide face in a lengthwise, axial direction of the blade or a ratio of a width of the second end surface in a lengthwise, axial direction of the blade to a width of the second guide face in a lengthwise, axial direction of the blade is 1:3 to 7, and
wherein a longitudinal axis of the plate-shaped blade is angled with respect to the central axis of the shank in the range of 30°-40°, the longitudinal axis and the central axis being on a plane which is parallel to the plate-shaped blade.

2. The stripping knife according to claim 1, wherein the handle has a substantially cylindrical shape.

* * * * *